United States Patent [19]

Mills et al.

[11] Patent Number: 5,252,567
[45] Date of Patent: Oct. 12, 1993

[54] DIAZINE DERIVATIVES

[75] Inventors: Stuart D. Mills, Macclesfield; Rodney B. Hargreaves, Poynton; Bernard J. McLoughlin, Macclesfield, all of Great Britain

[73] Assignee: Imperial Chemical Industries PLC, United Kingdom

[21] Appl. No.: 629,502

[22] Filed: Dec. 18, 1990

[30] Foreign Application Priority Data

Dec. 22, 1989 [GB] United Kingdom ............... 8929022

[51] Int. Cl.$^5$ ............... A61K 31/505; A61K 31/55; C07D 247/02; C07D 401/04
[52] U.S. Cl. ............... 514/211; 514/212; 514/218; 514/227.8; 514/235.8; 514/256; 514/275; 540/466; 540/467; 540/470; 540/481; 540/543; 540/544; 540/553; 540/575; 540/601; 544/60; 544/122; 544/230; 544/295; 544/296; 544/323; 544/326; 544/327; 544/329
[58] Field of Search ............ 514/211, 212, 218, 227.8, 514/235.8, 256, 275; 540/466, 467, 470, 481, 543, 544, 553, 575, 601; 544/295, 296, 323, 327, 326, 329, 230, 60, 122

[56] References Cited

U.S. PATENT DOCUMENTS

| | | | |
|---|---|---|---|
| 4,339,453 | 7/1982 | Grier et al. | 424/251 |
| 4,503,050 | 3/1985 | Wade | 514/222 |
| 4,514,398 | 4/1985 | Regnier et al. | 544/198 |
| 4,725,600 | 2/1988 | Takaya et al. | 514/269 |

FOREIGN PATENT DOCUMENTS

| | | |
|---|---|---|
| 47329/89 | 7/1990 | Australia . |
| 0090733 | 10/1983 | European Pat. Off. . |
| 0168262 | 7/1985 | European Pat. Off. . |
| 0243817 | 4/1987 | European Pat. Off. . |
| 3703633A1 | 8/1987 | Fed. Rep. of Germany . |
| 3629563A1 | 6/1988 | Fed. Rep. of Germany . |
| 87/01706 | 3/1987 | PCT Int'l Appl. . |
| 658205 | 10/1951 | United Kingdom . |
| 815833 | 7/1959 | United Kingdom . |
| 1020306 | 2/1966 | United Kingdom . |
| 2071092 | 9/1981 | United Kingdom . |

OTHER PUBLICATIONS

J. H. Forsberg, et al., "Homogeneous Catalysis Involving Lanthanoid (III) Ions: Formation of 4-Substituted-2,6-dimethylpyrimidines" *J. Chem. Soc. Chem. Comm.* (1976), 1060–1061.
Parnell, *Chem. Abstr.* (1963), 58, 1451e.
Tamada, *Chem. Abstr.* (1989), 111, 729, Abstr. 153334k.
Muravich, *Chem. Abstr.* (1973), 79, 425, Abstr. 105194a.
Kazantsev, *Chem. Abstr.* (1986), 105, 671, Abstr. 133849s.
Forsberg, *Chem. Abstr.* (1987), 106, 689, Abstr. 138408c.
Weinstock, *Chem. Abstr.* (1968), 69, 6290, Abstr. 67335f.
Ohno, *Chem. Abstr.* (1988), 108, 594, Abstr. 21816j.
Denny et al., *J. Med. Chem.* (1979), 22, 134–150.

Primary Examiner—Mark L. Berch
Attorney, Agent, or Firm—Cushman, Darby & Cushman

[57] ABSTRACT

This invention concerns compounds of the formula I:

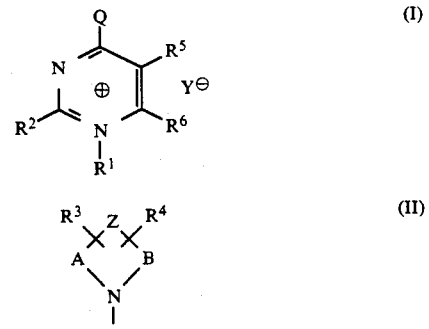

wherein $R^1$ is (1–10C)alkyl, (3–8C)cycloalkyl, (3–8C)cycloalkyl-(1–4C)-alkyl, phenyl or phenyl(1–4C)alkyl, the phenyl moiety of the latter two optionally bearing one or more substituents; $R^2$ is hydrogen, (1–4C)alkyl, amino or (1–4C)alkylamino; $R^6$ is (1–4C)alkyl, amino or (1–4C)alkylamino; Q is a group of formula II, in which case $R^3$ and $R^4$ are independently hydrogen, (1–4C)alkyl, phenyl or benzyl the phenyl moiety of the latter two optionally bearing one or two substituents; $R^5$ is hydrogen, (1–4C)alkyl or (2–4C)alkenyl; A and B are independently ethylene or trimethylene; Z is a direct bond between A and B, or an oxy, thio, carbonyl, methylene, ethylenedioxymethylene, ethylidene, or isopropylidene link, or Z is a group of the formula =N.M in which M is hydrogen, (1–6C)alkyl, phenyl or benzyl, the phenyl moiety of the latter two optionally bearing one or two substituents; or Q represents a saturated 9- or 10-membered bicyclic amino group, which is unsubstituted or is substituted by one or two substituents; and Y is a physiologically acceptable anion.

The invention also includes certain closely related anhydro-base derivatives which, like the compounds of formula I, possess beneficial effects on the cardiovascular system (and in particular beneficial effects modulated via the sino-atrial node). Also included are pharmaceutical compositions containing compounds of formula I (or a related anhydro-base) as active ingredient, and processes for the manufacture of the various novel compounds.

14 Claims, No Drawings

DIAZINE DERIVATIVES

This invention concerns novel diazine derivatives and, more particularly, novel cyclic amino pyrimidine derivatives which possess beneficial effects on the cardiovascular system, pharmaceutical compositions containing such a derivative as active ingredient, and processes for the manufacture of and medical use of the said derivatives.

Although numerous compounds are known to have medically useful effects on the cardiovascular system, hitherto there have not existed satisfactory agents which modulate the action of the sino-atrial node in warm-blooded animals such as man in a beneficial, selective and medically useful manner so that the agents are useful in treating cardiovascular disorders associated with an inappropriately elevated heart rate and yet have minimal effects on other haemodynamic parameters such as blood pressure or cardiac output. It is an object of the invention to provide such an agent.

Pyrimidine derivatives have been studied in the search for new pharmacologically active agents. For example, a series of aminopyrimidine derivatives has been described as having cardiotonic properties (U.S. Pat. No. 4,725,600). Various 4-aminopyrimidine salts have been described which are of potential use as antifungal and antibacterial agents (U.S. Pat. No. 4,339,453), and as trypanocides (UK 658,205). Bispyrimidinium compounds are also reported to possess trypanocidal activity (UK 1,020,306 and UK 815,833), and bisquaternary salts which include a pyrimidine moiety are reported to be useful as anti-tumour agents (Atwell et al, J. Med. Chem, Vol 22, No. 2, 1979, 134). The present invention is based on the unexpected and beneficial sino-atrial node modulatory effects of a novel series of aminopyrimidine deivatives of formula I as defined below.

According to the invention there is provided an amino pyrimidine derivative of the formula I (set out hereinafter, together with the other chemical formulae appearing herein in Roman numerals) wherein $R^1$ is (1-10C)alkyl, (3-8C)cycloalkyl, (3-8C)cycloalkyl-(1-4C)-alkyl, phenyl or phenyl(1-4C)alkyl, the phenyl moiety of the latter two optionally bearing one or more substituents independently selected from halogeno, (1-4C)alkyl, (3-6C)alkenyl, (1-4C)alkoxy, cyano, trifluoromethyl, nitro, amino, hydroxy, (1-4C)alkylamino, dialkylamino of up to six carbon atoms, (1-4C)alkylthio, (1-4C)alkylsulphinyl, (1-4C)alkylsulphonyl and (1-4C)alkylenedioxy; $R^2$ is hydrogen, (1-4C)alkyl, amino or (1-4C)alkylamino; $R^6$ is (1-4C)alkyl, amino or (1-4C)alkylamino; Q is a group of formula II, in which case $R^3$ and $R^4$ are independently hydrogen, (1-4C)alkyl, phenyl or benzyl the phenyl moiety of the latter two optionally bearing one or two substituents selected from (1-4C)alkyl, (1-4C)alkoxy and halogeno; $R^5$ is hydrogen, (1-4C)alkyl or (2-4C)alkenyl; A and B are independently ethylene or trimethylene; Z is a direct bond between A and B, or an oxy, thio, carbonyl, methylene, ethylenedioxymethylene, ethylidene, or isopropylidene link, or Z is a group of the formula =N.M in which M is hydrogen, (1-6C)alkyl, phenyl or benzyl, the phenyl moiety of the latter two optionally bearing one or two substituents selected from (1-4C)alkyl, (1-4C)alkoxy and halogeno; or Q represents a saturated 9-or 10-membered bicyclic amino group, which is unsubstituted or is substituted by one or two substituents selected from (1-4C)alkyl, phenyl or benzyl the phenyl moiety of the latter two optionally bearing one or two substituents selected from (1-4C)alkyl, (1-4C)alkoxy and halogeno; and Y is a physiologically acceptable anion.

It will be understood that when $R^2$ or $R^6$ is amino or alkylamino, the amino derivatives of the invention may exist in another tautomeric form to that depicted in formula I, or in a mixture of one or more of the possible tautomeric forms. It will also be understood that depending on the nature of the substituents, the compounds of the invention may contain a chiral centre and may exist in, and be isolated in, optically active or racemic form. The invention includes any tautomeric, optically active or racemic form of a compound of formula I which possesses the afore-mentioned beneficial pharmacological effects.

The compounds of formula I are quaternary salts and in some cases, for example, when $R^2$ or $R^6$ is amino or alkylamino, may be converted, for example by treatment with a quaternary ammonium hydroxide (and especially one in macroreticular resin form) to the corresponding neutral free bases of the formula IIIa or IIIb, respectively, in which $R^7$ is hydrogen or (1-4C)alkyl, or to a tautomeric form thereof depending on the nature of $R^2$ or $R^6$. Neutral free bases of the compounds of formula I, such as those of the formula IIIa or IIIb, are included as a further feature of the invention and may readily be reconverted to the quaternary salt form of formula I, for example, by treatment with the appropriate acid of the formula H.Y.

The term saturated 9- or 10-membered bicyclic amino group as used herein means a bicyclic amino group which is fully saturated and which is linked to the pyrimidine moiety through nitrogen.

A particular value for $R^1$ when it is alkyl is, for example, (1-6C)alkyl, such as methyl, ethyl, propyl or butyl, of which values methyl and ethyl are generally preferred.

A particular value for $R^1$ when it is cycloalkyl is, for example, cyclopentyl, cyclohexyl or cycloheptyl.

A particular value for $R^2$, $R^3$, $R^4$, $R^5$ or $R^6$ when it is alkyl is, for example, methyl or ethyl. A preferred value for $R^5$ is, for example, hydrogen.

A particular value for a substituent for the saturated azacarbobicyclic group (as defined above) when it is alkyl includes, for example, methyl or ethyl.

A particular value for $R^5$ when it is alkenyl is, for example, allyl, but-2-enyl or 2-methyl-2-propenyl.

A particular value for $R^1$ when it is cycloalkyl-alkyl is, for example, cyclopropyl-methyl, cylopentyl-methyl, cyclohexyl-methyl or 2-(cyclohexyl)ethyl.

A particular value for $R^1$ when it is phenylalkyl is, for example, benzyl, 1-phenylethyl or 2-phenylethyl, any of which may optionally be substituted as defined above.

A particular value for $R^2$ or $R^6$ when it is alkylamino is, for example, methylamino, ethylamino, propylamino or butylamino.

A particular value for M when it is alkyl is, for example, methyl, ethyl, propyl or butyl. A preferred value for M is, for example, methyl or phenyl.

Particular values for the group —A.Z.B— include, for example, tetramethylene, ethyleneoxyethylene [—CH$_2$CH$_2$.O.CH$_2$CH$_2$—], ethyleneoxytrimethylene [—CH$_2$CH$_2$.O.CH$_2$CH$_2$CH$_2$—], ethylenethioethylene [—CH$_2$CH$_2$.S.CH$_2$CH$_2$—], pentamethylene, hexamethylene, ethylenecarbonylethylene [—CH$_2$CH$_2$.CO.CH$_2$CH$_2$—]ethylene(ethylenedioxymethylene)ethylene and groups of the formula —CH$_2$CH$_2$.NR.CH$_2$CH$_2$— and —CH$_2$CH$_2$.NR.CH$_2$CH$_2$CH$_2$— in which R is methyl, ethyl, propyl, butyl or phenyl, the latter optionally bearing a substituent as defined for M above. Values of particular interest for substituents R$^3$ and R$^4$ on any of the above values of —A.Z.B— include, for example, when they are both hydrogen or methyl, or when one is hydrogen and the other is methyl, phenyl or benzyl (the phenyl moiety of the latter optionally substituted as defined above). Preferred values for substituents R$^3$ and R$^4$ on any of the above values of —A.Z.B— include, for example, when they are both methyl, or when one is hydrogen and the other is methyl, phenyl or benzyl (the phenyl moiety of the latter two optionally substituted as defined above).

Particular values for Q when it represents a saturated 9- or 10-membered bicyclic amino group include, for example, perhydroindolyl, perhydroquinolyl and perhydroisoquinolyl (unsubstituted or substituted as defined above).

Particular values for optional substituents which may be present on a phenyl moiety in R$^1$, R$^3$, R$^4$ or M as defined hereinabove include, by way of example:
for halogeno, fluoro, chloro and bromo;
for alkyl, methyl and ethyl;
for alkenyl, allyl;
for alkoxy, methoxy and ethoxy;
for alkylamino, methylamino and ethylamino;
for dialkylamino, dimethylamino and diethylamino;
for alkylthio, methylthio and ethylthio;
for alkylsulphinyl, methylsulphinyl and ethylsulphinyl;
for alkylsulphonyl, methylsulphonyl and ethylsulphonyl; and
for alkylenedioxy, methylenedioxy and isopropylidenedioxy.

In general, when R$^1$, R$^3$, R$^4$ or M contains a phenyl moiety it is preferably unsubstituted or else may bear one or two substituents.

Particular values for optional substituents which may be present on a phenyl moiety in a substituent for the saturated 9- or 10-membered bicyclic amino group defined hereinabove include, by way of example:
for halogeno, fluoro, chloro and bromo;
for alkyl, methyl and ethyl;
for alkoxy, methoxy and ethoxy;

In general, when Q represents a saturated 9- or 10-membered bicyclic amino group which bears a substituent which contains a phenyl moiety, the phenyl moiety is preferably unsubstituted or else may bear one or two substituents.

In general, when Q represents a saturated 9- or 10-membered bicyclic amino group (as defined above) it is preferred that the bicyclic amino group is unsubstituted.

By way of example it is generally preferred that R$^2$ and R$^6$ are not both basic groups, that is when R$^2$ is amino or alkylamino, R$^6$ is not amino or alkylamino.

In one embodiment of the invention Q represents a group of formula II (as defined above).

In a further embodiment of the invention Q represents a saturated 9- or 10-membered bicyclic amino group (as defined above).

In a particular embodiment of the present invention there is provided an amino pyrimidine derivative of the formula I (set out hereinafter, together with the other chemical formulae appearing herein in Roman numerals) wherein Q is a group of formula II; R$^1$ is (1–10C)alkyl, (3–8C)cycloalkyl, (3–8C)cycloalkyl-(1–4C)alkyl, phenyl or phenyl(1–4C)alkyl, the phenyl moiety of the latter two optionally bearing one or more substituents independently selected from halogeno, (1–4C)alkyl, (3–6C)alkenyl, (1–4C)alkoxy, cyano, trifluoromethyl, nitro, amino, hydroxy, (1–4C)alkylamino, dialkylamino of up to six carbon atoms, (1–4C)alkylthio, (1–4C)alkylsulphinyl, (1–4C)alkyl-sulphonyl and (1–4C)alkylenedioxy; R$^2$ is hydrogen, (1–4C)alkyl, amino or (1–4C)alkylamino; R$^3$ and R$^4$ are independently hydrogen, (1–4C)alkyl or phenyl, the latter optionally bearing one or two substituents selected from (1–4C)alkyl, (1–4C)alkoxy and halogeno; R$^5$ is hydrogen, (1–4C)alkyl or (2–4C)alkenyl; R$^6$ is (1–4C)alkyl, amino or (1–4C)alkylamino; A and B are independently ethylene or trimethylene; Z is a direct bond between A and B, or an oxy, thio, carbonyl, methylene, ethylenedioxymethylene, ethylidene, or isopropylidene link, or Z is a group of the formula =N.M in which M is hydrogen, (1–6C)alkyl, phenyl or benzyl, the phenyl moiety of the latter two optionally bearing one or two substituents selected from (1–4C)alkyl, (1–4C)alkoxy and halogeno; and Y is a physiologically acceptable anion.

Particular, preferred and specific values for R$^1$, R$^2$, R$^3$, R$^4$, R$^5$, R$^6$, A, B, Z, and M include the relevant values mentioned above.

By way of example, particular values for the group —A.Z.B— include, for example, tetramethylene, ethyleneoxyethylene [—CH$_2$CH$_2$.O.CH$_2$CH$_2$—], ethyleneoxytrimethylene [—CH$_2$CH$_2$.O.CH$_2$CH$_2$CH$_2$—], ethylenethioethylene [—CH$_2$CH$_2$.S.CH$_2$CH$_2$—], pentamethylene, hexamethylene, ethylenecarbonylethylene [—CH$_2$CH$_2$.CO.CH$_2$CH$_2$—] ethylene(ethylenedioxymethylene)ethylene and groups of the formula —CH$_2$CH$_2$.NR.CH$_2$CH$_2$— and —CH$_2$CH$_2$.NR.CH$_2$CH$_2$CH$_2$— in which R is methyl, ethyl, propyl, butyl or phenyl, the latter optionally bearing a substituent as defined for M above. Particular values for substituents R$^3$ and R$^4$ on any of the above values of —A.Z.B— include, for example, when they are both hydrogen or methyl, or when one is hydrogen and the other is methyl or phenyl (the latter optionally substituted as defined above).

Specific values for the group Q when Q is a group of formula II which are of particular interest include, for example, N-phenylpiperazino, N-(p-chlorophenyl)piperazino, piperidino, 3-methylpiperidino, 4-phenylpiperidino, 3,3-dimethylpiperidino, morpholino, hexamethyleneimino, 3-ethylpiperidino, 3,5-dimethylpiperidino, 3-n-propylpiperidino, 2-methylpiperidino, (4,4-ethylenedioxy)piperidino and p-methylphenylpiperidino.

Specific values for the group Q when Q is a saturated 9- or 10-membered bicyclic amino group which are of particular interest include, for example perhydro-1-indolyl, perhydro-1-quinolyl, and perhydro-2-isoquinolyl.

A group of compounds of the invention which is of interest comprises those compounds of the formula I wherein: R$^1$ is (1–4C)alkyl (especially methyl or ethyl), R$^6$ is (1–4C)alkyl (especially methyl or ethyl); R$^2$ is (1–4C)alkylamino (especially methylamino); Q is a 5–7 membered cyclic aliphatic amino group selected from pyrrolidino, morpholino, piperidino, N-phenylpiperazino, N-(halogenophenyl)piperazino, N-[(1–4C)alkylphenyl]piperazino, N-[(1–4C)alkoxyphenyl]piperazino, and hexamethyleneimino, any of which groups may itself optionally bear one or two substituents independently selected from methyl, ethyl, phenyl and halogenophenyl; and Y is a physiologically acceptable anion.

Specific values for the group Q which are of particular interest include, for example, 3-methylpyrrolidino, N-phenylpiperazino, N-(p-chlorophenyl)piperazino, piperidino, 3-methylpiperidino, 4-phenylpiperidino, 3,3-dimethylpiperidino, morpholino and hexamethyleneimino.

A preferred value for $R^1$ or $R^6$ is, for example, methyl.

A group of compounds of the invention which is of particular interest comprises those compounds of the formula IV wherein: Ra is (1–4C)alkyl (especially methyl or ethyl), Rb is (1–4C)alkyl (especially methyl or ethyl); Rc is (1–4C)alkyl (especially methyl); Q is a 5–7 membered cyclic aliphatic amino group selected from pyrrolidino, morpholino, piperazino, N-phenylpiperidino, N-(halogenophenyl)piperidino, N-[(1–4C)alkylphenyl]piperidino, N-[(1–4C)alkoxyphenyl]piperidino, hexamethyleneimino, any of which groups may itself optionally bear one or two substituents independently selected from methyl, ethyl, phenyl, benzyl and haolgenophenyl; or Q is a saturated 9- or 10-membered bicyclic amino group selected from perhydroindolyl, perhydroquinolyl and perhydroisoquinolyl, any of which groups may itself optionally bear one or two substituents independently selected from methyl, ethyl, phenyl, benzyl and haolgenophenyl; and Y is a physiologically acceptable anion.

Specific values for the group Q when Q is a group of formula II which are of particular interest include, for example, N-phenylpiperazino, N-(p-chlorophenyl)piperazino, piperidino, 3-methylpiperidino, 4-phenylpiperidino, 3,3-dimethylpiperidino, morpholino, hexamethyleneimino, 3-ethylpiperidino, 3,5-dimethylpiperidino, 3-n-propylpiperidino, 2-methylpiperidino, (4,4-ethylenedioxy)piperidino and p-methylphenylpiperidino.

Specific values for the group Q when Q is a saturated 9- or 10-membered bicyclic amino group which are of particular interest include, for example perhydro-1-indolyl, perhydro-1-quinolyl, and perhydro-2-isoquinolyl.

A preferred value for Ra, Rb or Rc is, for example, methyl.

Particular physiologically acceptacle counter anions Y include, for example, halide (such as chloride, bromide or iodide), sulphate, phosphate, nitrate, acetate, citrate, fumarate, succinate, trifluoroacetate, methosulphate and p-toluenesulphonate.

A preferred group of free bases of the invention defined above comprises those compounds of the formula IVa in which Ra, Rb, Rc and Q have any of the meanings defined above.

The compounds of the invention are illustrated by the accompanying Examples, of which the compounds described in Examples 1, 2, 5, 6, 7, 8, 9, 10, 13, 15, 16, 18, 21, 22, 23, 24 and 26 are of of particular interest, and those described in Examples 1, 2, 5, 8, 9, 10, 13, 15, 22, 23 and 26 are of special interest. The latter compounds, as described herein or in the form of a salt with an alternative physiologically acceptable counter anion, are provided as a further feature of the invention.

The compounds of the invention may be obtained by standard procedures of organic chemistry already known to be applicable to the preparation of structurally analogous compounds, for example those procedures described in standard reference works on the chemistry of the pyrimidines. Such procedures for the manufacture of the novel compounds of formula I are provided as a further feature of the invention and are illustrated by the following preferred processes in which the various generic radicals have any of the meanings defined hereinbefore.

a) An amino pyrimidine of the formula V is reacted with an alkylating agent of the formula $R^8.L$ in which L is a suitable leaving group and $R^8$ has the same meanings as $R^1$ except phenyl, substituted phenyl as defined above or cycloalkyl.

A preferred value for L is, for example, halide (especially iodide, bromide or chloride), p-toluenesulphonate or a group of the formula $—O.SO_2.OR^8$.

The reaction is generally carried out by heating the alkylating agent with the compound of formula V at a temperature of, for example, 40°–120° C. and is conveniently carried out in a suitable solvent or diluent, for example, in an ether such as dioxane, tetrahydrofuran or t-butyl methyl ether. Where the leaving group L is not the required counterion Y in the required compound of formula I, it may readily be exchanged by standard techniques mentioned hereinafter.

The starting materials of formula V can be made, for example, by reaction of the corresponding halogenopyrimidine of the formula VI wherein X is chloro or bromo with the appropriate cyclic amine of the formula IX or the appropriate 9- or 10-membered bicyclic amine at a temperature in the range, for example, 40°–150° C. This particular reaction may be carried out in the presence of a suitable solvent or diluent such as a (1–4C)alkanol or N,N-dimethylformamide, or as a melt of the reagents alone. The amines of the formula IX and the 9- or 10-membered bicyclic amines, and the compounds of formula VI are in general known or may be made by conventional techniques well known in the art of organic and heterocyclic chemistry.

Although it will be appreciated that in principle it is possible for alkylation to occur on either of the endocyclic nitrogen atoms, in practice alkylation takes place predominantly on the nitrogen shown bearing $R^1$ in formula I and any small amount of the alternative isomer may be removed by well known methods for the purification of organic compounds, for example by chromatographic means or by fractional crystallisation. The position of alkylation can be established by standard techniques, for example by studies of the nuclear Overhauser effect on the proton magnetic resonance of the sample concerned.

b) Reacting a pyrimidinium salt of the formula VII wherein X is a suitable leaving group with an amine of the formula IX or the appropriate 9- or 10-membered bicyclic amine.

Y is an appropriate counter-ion.

The process will be seen to be analogous to that described above for the production of the starting materials of the formula V and analogous conditions may in general be used. Thus, the process is generally carried out at an elevated temperature in the range, for example, 20°–150° C. and in the presence of a suitable solvent or diluent such as a (1–4C)alkanol or N,N-dimethylformamide.

A particularly suitable leaving group X is, for example, halogeno (especially chloro or bromo), dichlorophosphinoyl $[—O.PO.Cl_2]$, or dibromophosphinoyl $[—O.PO.Br_2]$. The latter two groups may conveniently be introduced in situ by the reaction of the corresponding pyrimidinone with phosphorus oxychloride or oxybromide, respectively.

The pyrimidinium salts of formula VII (except those wherein $R^1$ is phenyl, substituted phenyl or cycloalkyl) may alternatively be obtained, for example, by analogy with process (a) above, that is by reaction of a halogenopyrimidine of the formula VI with the appropriate alkylating agent of the formula $R^8.L$ and, in particular, with an iodide or bromide of the formula $R^8.I$ or $R^8.Br$.

The 1-substituted pyrimidin-4-ones may themselves be obtained by standard procedures of heterocyclic chemistry well known in the art. This procedure is particularly suitable for the production of salts of formula VII in which $R^1$ is phenyl, substituted phenyl and cycloalkyl.

c) For those compounds wherein $R^6$ is amino or alkylamino, reacting a pyrimidium salt of formula VIII wherein X is a suitable leaving group with the appropriate amine selected from ammonia and (1–4C)alkylamine, or a salt thereof with a (1–4C)alkanoic acid (such as acetic acid).

Y is an appropriate counter-ion.

The process will be seen to be analogous to process (b) described above and analogous considerations and reaction conditions may in general be used. In general an excess of the starting amine or an alkanoic acid salt thereof will be used. The starting compounds of formula VIII may be obtained in a generally similar manner to those for formula VII compounds.

It will be appreciated that the counter anion $Y^-$ may readily be changed, for example, by reaction of the compound of formula I with a suitable salt such as a silver salt or by ion-exchange chromatography on a column of a basic macroreticular resin in the form of its salt with the desired counter anion, or another conventional method.

When a neutral compound of formula IIIa, IIIb or IVa is required, it may be obtained, for example, by reaction of the appropriate compound of formula I in which $R^2$ or $R^6$ is amino or alkylamino, with a strong base such as macroreticular resin containing quaternary ammonium hydroxide groups. The process is conveniently carried out by exposing a solution of the compound of formula I in an aqueous solvent such as an aqueous (1–4C)alkanol (for example methanol, ethanol or 2-propanol) to the resin at or near ambient temperature, for example by trickling the solution over a bed or through a column of the resin.

It will also be appreciated that certain of the various optional substituents in the compounds of the invention may be introduced by standard aromatic substitution reactions or generated by conventional functional group modifications either prior to or immediately following process (a), (b) or (c) above. Such reactions and modifications include, for example, introduction of nitro or halogeno, reduction of a nitro, reductive alkylation of nitro, oxidation of alkylthio to alkylsulphinyl or alkylsulphonyl and reduction of alkynyl or alkenyl. The reagents and reaction conditions for such procedures are well known in the chemical art.

Many of the intermediates are novel and are provided as a further feature of the present invention. In particular the present invention also provides a compound of formula V, wherein Q, $R^2$, $R^5$ and $R^6$ may have any of the meanings given above.

As indicated above, the compounds of the invention possess useful pharmacological properties and modulate the action of the sino-atrial node in warm-blooded animals in a beneficial, selective and medically useful manner so that the agents are useful in treating cardiovascular disorders associated with an inappropriately elevated heart rate and with minimal effects on other haemodynamic parameters such as blood pressure or cardiac output. The beneficial and selective effects of the cardiovascular system may be demonstrated using the following standard laboratory techniques.

a) Bradycardic effect (reduction in beating rate of the spontaneously beating isolated guinea pig right atrium).

This technique involves the dissection of the right atrium from a guinea pig heart, taking care not to damage the sino-atrial node region. The atrium is established in oxygenated (95% $O_2$; 5% $CO_2$) Tyrode's solution [containing 8.0 g NaCl, 0.19 g KCl, 0.025 g $MgCl_2$, 0.05 g $NaH_2PO_4$, 0.2 g $CaCl_2$ and 2.7 g glucose, per liter of deionised water] between two platinum spikes which are connected via an amplifier to a conventional ratemeter, triggered by the action potentials across the atrium. The preparation is bathed in oxygenated Tyrode's solution at 37 degrees Celsius and allowed to equilibrate for 30 minutes before the addition of a solution of the test compound in a mixture of dimethyl sulphoxide and Cremophor EL, diluted as required with Tyrode's solution. Further solutions of test compound are then added cumulatively at 15 minute intervals or when a steady-state beating rate has been attained. This enables an $IC_{20}$ (i.e. the micromolar concentration required to reduce the beating rate by 20%) to be calculated. Typically, a compound of formula I will have an $IC_{20}$ of 10 micromolar or less.

b) Effect on contractile force of electrically stimulated isolated guinea pig left atrium.

This technique involves the dissection of the left atrium from a guinea pig heart into oxygenated Tyrodes solution. The atrium is then clamped in an polyacrylate plastic holder containing two stainless steel stimulating electrodes. The free end of the atrium (normally the atrial appendage) is attached with silk thread to an isometric force transducer. The atrium is then set under a resting tension of 1 g and is allowed to equilibrate in oxygenated Tyrode's solution for 20 minutes before being stimulated into beating by application of 2.5 Hz, 3 mS pulses at 1.5 times the threshold voltage (normally in the range 3–7 V). A solution ($10^{-5}M$ or less) of the test compound [made up as in (a) above] is then added and the effect on contractile force measured. In this way a comparison of the effect with that of a control solution without any test compound can be obtained. Typically, at a concentration in the range 1–30 micromolar compounds of the formula I show <15% reduction in contractile force.

c) Bradycardic effect in the anaesthetised rat

This technique involves the use of Wistar rats (Alderley Park strain) which are pre-anaesthetised by intravenous injection of alphaxalone/alphadalone (1.5 ml per kg). A polyethylene cannula is inserted into the jugular vein and anaesthesia is maintained by infusion of alphaxalone/alphadalone at a rate of 0.025–0.12 ml per kg per minute. A polyethylene cannula is also inserted into the carotid artery and connected to a pressure transducer filled with physiological saline solution. The arterial blood pressure signal is used to trigger an internally calibrated heart rate meter and the transducer is calibrated with a mercury manometer. The output of the heart rate meter and of the pressure transducer are then recorded simultaneously on a standard chart recorder.

After cannulation, the rat preparation is allowed to stabilise for 10 minutes. A solution of a test compound [made up as in (a) above, in a volume of 1 ml per kg] is then administered via the venous cannula in four cumulative doses separated by 5 minute intervals. A group of five rats is used for each test compound. The effects on heart rate and blood pressure may then be determined in comparison with those of a control injection.

Typically, a compound of formula I active using this procedure will require an i.v. dose of 5 mg/kg or less to produce a 30% reduction in heart rate (i.e. the $ED_{30}$ dose).

The beneficial effects of a test compound on the cardiovascular system, such as bradycardic effects without an adverse effect on heart force, blood pressure and or cardiac output, may also be determined in anaesthetised dogs and in dogs in which tachycardia has been induced by exercise. In general, the compounds of the invention show significant and predominantly selective bradycardic effects as evidenced by activity in at least two of the above mentioned test techniques. No overt toxicity is generally observed with the compounds of formula I in the above in vivo test techniques at doses several multiples of those at which significant bradycardic effects are seen.

By way of illustration, the compound described hereinafter in Example 1 had an $IC_{20}$ of about $10^{-6}M$ in procedure (a) and had an $ED_{30}$ of about 2 mg/kg i.v. for reduction of heart rate in procedure (c). Other compounds of formula I, such as those exemplified hereinafter, will typically show activity of the same general order.

As mentioned above the compounds of the present invention are of potential use in treating diseases of the cardiovascular system. Thus there is also provided a compound of the present invention (as defined above) for use in therapy, and the use of a compound of the present invention for the manufacture of a medicament for treating cardiovascular disease. The present invention also provides a method of modulating the action of the sino-atrial node in a warm-blooded animal, such as man, requiring such treatment which method comprises administering an effective amount of a compound of the present invention (as defined above).

When used in the treatment of diseases of the cardiovascular system, such as myocardial ischaemia affecting warm-blooded animals (and in particular man), it is envisaged that a compound of formula I will be administered orally, intravenously or by some other medically acceptable route (such as by inhalation, insufflation, sub-lingual or transdermal means) so that a dose in the general range, for example, 0.01 mg to 10 mg per kg body weight is received. However, it will be understood that the precise dose administered will necessarily vary according to the nature and severity of the disease and the age and sex of the patient being treated.

In general, the compounds of formula I will usually be administered in the form of a pharmaceutical composition, that is, together with a pharmaceutically acceptable diluent or carrier and such a composition is provided as a further feature of the invention and may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; in the form of a powder, together with pharmaceutically acceptable inert solid diluents such as lactose, for administration by insufflation; or in the form of a skin patch for transdermal administration. The compositions may conveniently be in unit dose form containing, for example, 5–200 mg of the compound of formula I.

The compositions may be obtained by conventional procedures using pharmaceutically acceptable diluents and carriers well known in the art. Tablets and capsules for oral administration may conveniently be formed with an enteric coating (such as one based on cellulose acetate phthalate) to minimise contact of the active ingredient of formula I with stomach acids.

The compositions of the invention may also contain one or more agents known to be of value in the diseases or conditions of the cardiovasculature intended to be treated. Thus, they may contain, in addition to the compound of formula I, for example, a known platelet aggregation inhibitor, prostanoid constrictor antagonist or synthase inhibitor (thromboxane $A_2$ antagonist or synthase inhibitor), cyclooxygenase inhibitor, hypolipidemic agent, anti-hypertensive agent, inotropic agent, beta-adrenergic blocker, thrombolytic agent or a vasodilator.

In addition to their use in therapeutic medicine, the compounds of formula I are also useful as pharmacological tools in the development and standardisation of test systems for the evaluation of the new cardiovascular agents in laboratory animals such as cats, dogs, rabbits, monkeys, rats and mice.

The invention will now be illustrated by the following non-limiting Examples in which, unless otherwise stated (i) evaporations were carried out by rotary evaporation in vacuo;

(ii) operations were carried out at room temperature, that is in the range 18°–26° C.;

(iii) flash column chromatography or medium pressure liquid chromatography (MPLC) was performed on silica gel [either Fluka Kieselgel 60 (catalogue no. 60738) obtained from Fluka AG, Buchs, Switzerland, or Merck Kieselgel Art. 9385, obtained from E Merck, Darmstadt, Germany];

(iv) yields are given for illustration only and are not necessarily the maximum attainable by diligent process development;

(v) proton NMR spectra were normally determined at 200 MHz in deuterated dimethyl sulphoxide as solvent, using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet;

(vi) conventional abbreviations are used for recrystalisation solvents, for example EtOAc for ethyl acetate, EtOH for ethanol, $Et_2O$ for diethyl ether, IPA for 2-propanol and DMF for N,N-dimethylformamide; and (vii) end-products had satisfactory microanalysis, NMR and/or mass spectroscopy.

EXAMPLE 1

A mixture of 2-methyl-6-methylamino-4-(4-phenylpiperidino)pyrimidine (564 mg; 2 mM) and methyl iodide (1 ml; 16 mM) in dioxan (10 ml) was heated under reflux for 15 hours. The mixture was cooled, the solvent removed in vacuo and the residue was crystallised from a mixture of methanol and ether. There was thus obtained 1,2-dimethyl-6-methylamino-4-(4-phenyl-piperidino)pyrimidinium iodide (506 mg, 60% yield) m.p. 193°-196° C.; microanalysis found: C,50.6; H,5.8; N,12.9%; $C_{18}H_{25}N_4I$ reqiures C,50.9; H,5.9; N,13.2%; NMR (200 MHz, $d_6$-DMSO): 1.45-1.75 (2H, octet, piperidine 3-H axial and 5-H axial), 1.85-2.00 (2H,d, piperidine 3-H equatorial and 5-H equatorial), 2.55-2.60 (3H,s, $CH_3$), 2.85-2.95 (3H, d, $NHCH_3$), 3.00-3.20 (3H, br, piperidine 2-H axial and 6-H axial), 3.45-3.55 (3H, s, N—$CH_3$), 4.4-4.8 (2H, br, piperidine 2-H equatorial and 6-H equatorial), 5.8-5.85 (1H, s, pyrimidine 5-H), 7.15-7.40 (5H, complex, aromatic), 7.7-7.85 (1H,q, NH).

[Note: the site of quaternisation was confirmed by conventional Nuclear Overhauser studies].

The pyrimidine starting material was prepared as follows:

A mixture of 4-chloro-2-methyl-6-methylaminopyrimidine (525 mg, 3.3 mM; described in *J. Pharm. Soc.* (Japan) 1966, 86, p. 952) and 4-phenylpiperidine (1.08 g, 6.6 mM) was heated as a melt at 135°-140° C. for 1 hour. The residue, obtained after cooling, was triturated with ether and the mixture separated by filtration. The solid was suspended in a mixture of 50% w/v potassium hydroxide solution (50 ml) and isopropanol (50 ml). The mixture was heated under reflux for 2 hours and cooled. The organic layer was separated and the solvent removed in vacuo. The residue was dissolved in methylene chloride (50 ml), washed with water (2×25 ml), dried ($MgSO_4$) and the solvent evaporated. The residue was purified by flash chromatography on silica (Merck Art. 9385, 100 g), using a mixture of methanol and methylene chloride (1:9 v/v) as eluant, to give 2-methyl-6-methylamino-4-(4-phenylpiperidino)-pyrimidine (700 mg, 75% yield), m.p. 186°-188° C.; microanalysis, found: C, 71.6; H,7.5; N,19.3%; $C_{17}H_{22}N_4·\frac{1}{4}H_2O$ requires C,71.2; H,7.8; N,19.5%.

EXAMPLES 2-11

The procedure described in Example 1 was repeated using the appropriate 4-(substituted amino)pyrimidine of formula V and methyl iodide. There were thus obtained the following compounds of formula I; ($R^1=R^2$=methyl, $R^5$=H, $R^6$=methylamino)

| Example | Q | Purification* | m.p. (°C.) | Yield (%) |
|---|---|---|---|---|
| 2 | N-phenylpiperazino | a | 250-252 | 53 |
| 3 | N-p-chlorophenyl-piperazino | a | 260-262 | 58 |
| 4 | 4-p-chlorophenyl-piperidino | b | 192-193 | 46 |
| 5 | piperidino | c | 208-210 | 33 |
| 6 | morpholino | c | 215-218 | 55 |
| 7 | hexamethyleneimino | c | 208.5-209 | 72 |
| 8 | 3,3-dimethylpiperidino | c | 183.5-184 | 44 |
| 9 | 3-methylpiperidino | c | 180-181 | 32 |
| 10 | 2-methylpiperidino | c | 179-179.5 | 34 |
| 11 | (4,4-ethylenedioxy)-piperidino | a | 261-262 | 53 |

The starting pyrimidines of formula V ($R^2$=methyl, $R^5$=H, $R^6$=methylamino) were made in an analogous manner to that described for the starting material of Example 1 and had the following properties:

| Compound No. | Q | Purification* | m.p. (°C.) | Yield (%) |
|---|---|---|---|---|
| 1 | N-phenylpiperazino | a | 174-178 | 44 |
| 2 | N-p-chlorophenyl-piperazino | a | 207-209 | 69 |
| 3 | 4-p-chlorophenyl-piperidino | b | 207-208.5 | 25 |
| 4 | piperidino | a | 131-135 | 65 |
| 5 | morpholino | a | 185-187 | 88 |
| 6 | hexamethyleneimino | c | 127-128 | 60 |
| 7 | 3,3-dimethylpiperidino | c | 118.5-119 | 53 |
| 8 | 3-methylpiperidino | d | 99-102 | 51 |
| 9 | 4-methylpiperidino | d | 102-102.5 | 61 |
| 10 | 2-methylpiperidino | c | 125-125.5 | 38 |
| 11 | (4,4-ethylenedioxy)-piperidino | c | 150-150.5 | 72 |

*Purification by:
a column chromatography without recrystallisation;
b recrystallisation from ethanol;
c recrystallisation ethyl acetate; or
d recrystallisation from hexane.

EXAMPLE 12

A column of quaternary ammonium hydroxide anion exchange resin was made up from Amberlite* IRA400 (hydroxide form) (50 mm long×10 mm diameter) in deionised water. The bed of the resin was washed with 20% v/v ethanol/water (120 ml) (eluate pH=7). A mixture of 1,2-dimethyl-6-methylamino-4-(3-methyl-piperidino)pyrimidinium iodide (250 mg) and 20% v/v ethanol/water (5 ml) was then loaded on to the column and elution was carried out using 20% v/v ethanol/water (100 ml). The fractions containing the product were evaporated and the residue was dissolved in deionised water (15 ml) (Solution pH=12). The pH of the solution was adjusted carefully to 6.7 by addition of 0.1M hydrochloric acid and the mixture was evaporated to dryness. The residue was crystallised from a mixture of methanol and ethyl acetate and there was thus obtained 1,2-dimethyl-6-methylamino-4-(3-methylpiperidino)-pyrimidinium chloride (121 mg, 65% yield), m.p. 213°-215° C.; microanalysis, found: C, 57.0; H, 8.6; N, 20.3; Cl, 13.5%; $C_{13}H_{23}ClN_4·0.2H_2O$ requires C, 56.9; H, 8.5; N, 20.4; Cl, 13.0%; NMR: 0.90 (3H, d, $CH_3$), 1.10-1.90 (5H, complex, piperidine $CHCH_3$, $CH_2CH_2$), 2.55 (3H, s, $CH_3$), 2.75 (1H, t, piperidine 2-H axial or 6-H axial), 2.85 (3H, s, $NHCH_3$), 3.05 (1H, t, piperidine 2-H axial or 6-H axial), 3.50 (3H, s, N-$CH_3$), 4.20-4.50 (2H, broad, piperidine 2-H equatorial and 6-H equatorial), 5.75 (1H, s, pyrimidine 5H), 8.05 (1H, broad singlet, NH)
[*Amberlite is a trade mark, the property of the Rohn and Haas Co.].

EXAMPLE 13

A mixture of 2-amino-4-chloro-1,6-dimethyl-pyrimidinium iodide (0.571 g; 2 mM; described in *Indian Research*, 1976, 21 p. 96) and 4-phenylpiperidine (0.644 g; 4 mM) in ethanol (30 ml) was heated under reflux for 15 hours. The solvent was removed in vacuo and the residue was triturated with ether. The solid was removed by filtration and recrystallised from a mixture of methanol and ether to give 2-amino-1,6-dimethyl-4-(4-phenylpiperidino)pyrimidinium iodide as a solid (0.41 g, 50% yield), m.p. 248°-250° C. (decomp.); microanalysis, found: C,50.0; H,5.6; N,13.7%; $C_{17}H_{23}N_4I$ requires C,49.8; H,5.6; N,13.7%; NMR (220 MHz; $d_5$): 1.4-1.75 (2H, b, piperidine 3-H axial and 5-H axial), 1.85-2.0 (2H, d, piperidine 3-H equatorial and 5-H equatorial), 2.4 (3H, s, $CH_3$), 2.8-3.3 (3H, b, piperidine 4-H and piperidine 2-H axial and 6-H axial), 3.45 (3H, s, N—CH₃), 4.2–4.4 (1H, broad d, piperidine 2-H equatorial or 6-H equatorial), 4.85–5.05 (1H, broad d, piperidine 6-H equatorial or 2-H equatorial), 6.7 (1H, s pyrimdine 5H), 7.1–7.4 (5H, complex, aromatic H), 7.85–8.0 (2H, br, NH₂).

EXAMPLES 14–23

The procedure described in Example 1 was repeated using the appropriate 4-substituted pyrimidine of formula V and methyl iodide. There was thus obtained the following compounds of formula I ($R^1$=methyl, $R^5$=H)

| EX. | Q | $R^2$ | $R^6$ | m.p. (°C.) | Purification* | Yield (%) |
|---|---|---|---|---|---|---|
| 14 | 4-p-methyl-phenyl-piperidino | Me | —NHMe | 192–193 | a | 33 |
| 15 | 3-ethyl-piperidino | Me | —NHMe | 177–178 | a | 44 |
| 16 | S-(+)-3-methyl-piperidino | Me | —NHMe | 187–189 | a | 35 |
| 17 | R-(−)-3-methyl-piperidino | Me | —NHMe | 189–190 | a | 42 |
| 18 | cis-3,5-di-methyl-piperidino | Me | —NHMe | 260–261.5 | a | 47 |
| 19 | 3-n-propyl-piperidino | Me | —NHMe | 179–181 | a | 48 |
| 20 | 3-benzyl-piperidino | Me | —NHMe | 173–175 | a | 17 |
| 21 | 3-methyl-piperidino | Me | —NHEt | 176.5–177.5 | b | 46 |
| 22 | 3-methyl-piperidino | Et | —NHMe | 177–178 | c | 27 |
| 23 | 3-methyl-piperidino | Et | —NHEt | 163–164 | b | 22 |

*Purification by:-
a recrystallisation from methanol/ethyl acetate.
b recrystallisation from ethyl acetate.
c recrystallisation from ethanol/ethyl acetate.

The starting pyrimidines of formula V ($R^2$=methyl, $R^5$=H) we made in an analogous manner to that described for the starting material of Example 1 and had the following properties:

| Compound No | Q | R2 | R6 | M.p. (°C.) | Purification* | Yield (%) |
|---|---|---|---|---|---|---|
| 14 | 4-p-methyl-phenyl-piperidino | Me | —NHMe | 190–192 | a | 35 |
| 15 | 3-ethyl-piperidino | Me | —NHMe | 104–106 | b | 48 |
| 16 | S-(+)-3-methyl-piperidino | Me | —NHMe | 99–101 | b | 51 |
| 17 | R-(−)-3-methyl-piperidino | Me | —NHMe | 99–101 | b | 57 |
| 18 | cis-3,5-di-methyl-piperidino | Me | —NHMe | 161.5–162.5 | c | 41 |
| 19 | 3-n-propyl-piperidino | Me | —NHMe | 106–108 | b | 43 |
| 20 | 3-benzyl-piperidino | Me | —NHMe | 119–120 | b | 39 |
| 21 | 3-methyl-piperidino | Me | —NHEt | 77–78 | b | 54 |
| 22 | 3-methyl-piperidino | Et | —NHMe | 83.5–84.5 | d | 29 |
| 23 | 3-methyl-piperidino | Et | —NHEt | 196–197[1] | a | 10 |
| | piperidino | | | | | |

([1] characterised as the hydrochloride salt).
*Purification by:
a recrystallisation from ethanol
b recrystallisation from n-hexane
c recrystallisation from ethyl acetate
d recrystallisation from aqueous methanol Note: 6-chloro-2-methyl-4-ethylaminopyrimidine used to prepare 21 was obtained as described by H Gershon et alia. J. Hed. Chem. 1964, 7, 808, and the corresponding intermediates for compounds 22 and 23 were obtained essentially pure by the same method as oils and were used directly without characterisation. 3-Methylpiperidine was resolved into its enantiomers as described by G Bettoni et alia. Gazzetta. Chim. Ital. 1972, 102, 196.

EXAMPLES 24–27

The procedure described in Example 1 was repeated using the appropriate 4-substituted pyrimidine of formula V and methyl iodide. There were thus obtained the following compounds of formula I ($R^1$=$R^2$=methyl; $R^5$=H; $R^6$=methylamino).

| Example | Q | | m.p. (°C.) | Purification* | Yield (%) |
|---|---|---|---|---|---|
| 24 | cis/trans | 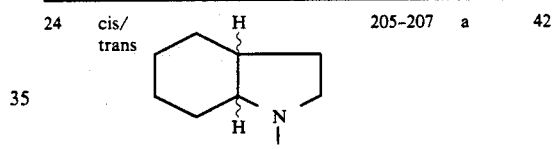 | 205–207 | a | 42 |
| 25 | trans | 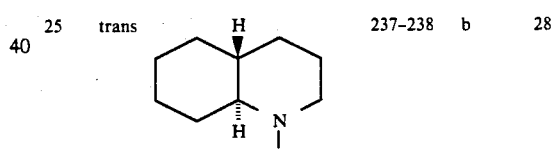 | 237–238 | b | 28 |
| 26 | trans | 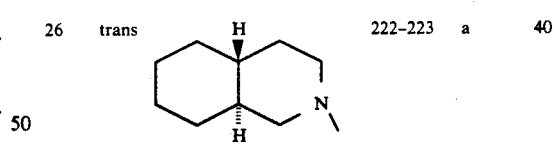 | 222–223 | a | 40 |
| 27 | cis | 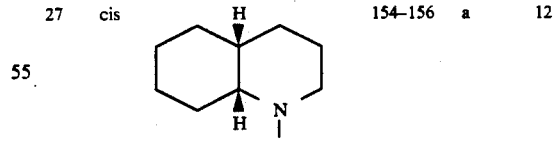 | 154–156 | a | 12 |

*Purification by: -
a) recrystallisation from methanol/ethyl acetate.
b) recrystallisation from ethanol.
Note: The compound described in Example 24 is a mixture of cis and trans isomers.

The starting pyrimidines of formula V ($R^2$=methyl; $R^5$=H; $R^6$ methylamino) were made in an analogous manner to that described for the starting material of Example 1 and had the following properties:

| Compound No. | Q | m.p. (°C.) | Purification* | Yield (%) |
|---|---|---|---|---|
| 24 | 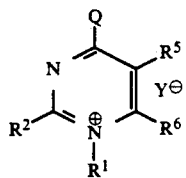 | 149–150 | a | 64 |
| 25 trans | 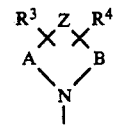 | 158–159 | b | 16 |
| 26 trans | 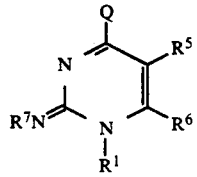 | 173–174.5 | c | 62 |
| 27 cis | 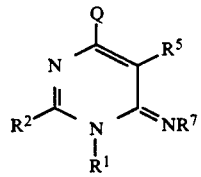 | 145–147 | b | 39 |

*Purification by: -
a) recrystallisation from ethyl acetate/n-hexane.
b) recrystallisation from ethyl acetate.
c) recrystallisation from ethanol.

Note: The starting material for compound 24 was a mixture of cis- and trans-perhydroindole as supplied by the Aldrich Chemical Company Ltd.

EXAMPLE 28

The following illustrate representative pharmaceutical dosage forms containing a compound of formula I, for example as illustrated in any of the previous Examples, (hereafter referred to as "compound X"), for therapeutic or prophylactic use in humans:

| (a) Tablet | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (b) Capsule | mg/capsule |
|---|---|
| Compound X | 10 |
| Lactose Ph.Eur | 488.5 |
| Magnesium stearate | 1.5 |

The above formulations may be obtained by conventional procedures well known in the pharmaceutical art. If required, the tablets may be enteric coated by conventional means, for example, to provide a coating of cellulose acetate phthalate.

CHEMICAL FORMULAE

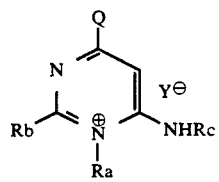 (I)

(II)

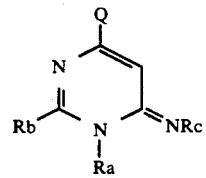 (IIIa)

(IIIb)

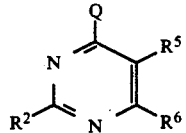 (IV)

(IVa)

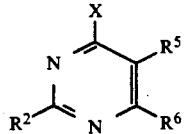 (V)

(VI)

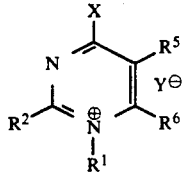 (VII)

-continued
CHEMICAL FORMULAE

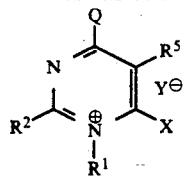
(VIII)

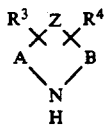
(IX)

We claim:
1. An amino pyrimidine derivative of formula I

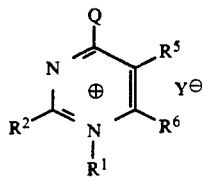
(I)

wherein $R^1$ is (1–10C)alkyl, (3–8C)cycloalkyl, (3–8C)cycloalkyl-(1–4C)alkyl, phenyl or phenyl(1–4C)alkyl, the phenyl moiety of the latter two optionally bearing one or more substituents independently selected from halogeno, (1–4C)alkyl, (3–6C)alkenyl, (1–4C)alkoxy, cyano, trifluoromethyl, nitro, amino, hydroxy, (1–4C)alkylamino, dialkylamino of up to six carbon atoms, (1–4C)alkylthio, (1–4C)alkylsulphinyl, (1–4C)alkylsulphonyl and (1–4C)alkylenedioxy; $R^2$ is hydrogen, (1–4C)alkyl, amino or (1–4C)alkylamino; $R^6$ is (1–4C)alkyl, amino or (1–4C)alkylamino; Q is a group of formula II,

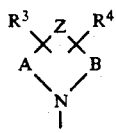
(II)

in which case $R^3$ and $R^4$ are independently hydrogen, (1–4C)alkyl, phenyl or benzyl, the phenyl moiety of the latter two optionally bearing one or two substituents selected from (1–4C)alkyl, (1–4C)alkoxy and halogeno; $R^5$ is hydrogen, (1–4C)alkyl or (2–4C)alkenyl; A and B are independently ethylene or trimethylene; Z is a direct bond between A and B, or an oxy, thio, carbonyl, methylene, ethylenedioxymethylene, ethylidene, or isopropylidene link, or Z is a group of the formula =NM in which M is hydrogen, (1–6C)alkyl, phenyl or benzyl, the phenyl moiety of the latter two optionally bearing one or two substituents selected from (1–4C)alkyl, (1–4C)alkoxy and halogeno; or Q represents a fully saturated 9- or 10-membered bicyclic ring system containing one nitrogen as the only heteroatom, Q being attached through said nitrogen to the remainder of said amino pyrimidine derivative, which Q is unsubstituted or is substituted by one or two substituents selected from (1–4C)alkyl, phenyl or benzyl, the phenyl moiety of the latter two optionally bearing one or two substituents selected from (1–4C)alkyl, (1–4C)alkoxy and halogeno; and Y is a physiologically acceptable anion.

2. A compound as claimed in claim 1 wherein Q is a group of formula II; $R^1$ is (1–10C)alkyl, (3–8C)cycloalkyl, (3–8C)-cycloalkyl-(1–4C)alkyl, phenyl or phenyl(-1–4C)alkyl, the phenyl moiety of the latter two optionally bearing one or more substituents independently selected from halogeno, (1–4C)alkyl, (3–6C)alkenyl, (1–4C)alkoxy, cyano, trifluoromethyl, nitro, amino, hydroxy, (1–4C)alkylamino, dialkylamino of up to six carbon atoms, (1–4C)alkylthio, (1–4C)alkylsulphinyl, (1–4C)alkylsulphonyl and (1–4C)alkylenedioxy; $R^2$ is hydrogen, (1–4C)alkyl, amino or (1–4C)alkylamino; $R^3$ and $R^4$ are independently hydrogen, (1–4C)alkyl or phenyl, the latter optionally bearing one or two substituents selected from (1–4C)alkyl, (1–4C)alkoxy and halogeno; $R^5$ is hydrogen, (1–4C)alkyl or (2–4C)alkenyl; $R^6$ is (1–4C)alkyl, amino or (1–4C)alkylamino; A and B are independently ethylene or trimethylene; Z is a direct bond between A and B, or an oxy, thio, carbonyl, methylene, ethylenedioxymethylene, ethylidene, or isopropylidene link, or Z is a group of the formula =NM in which M is hydrogen, (1–6C)alkyl, phenyl or benzyl, the phenyl moiety of the latter two optionally bearing one or two substituents selected from (1–4C)alkyl, (1–4C)alkoxy and halogeno; and Y is a physiologically acceptable anion.

3. A compound as claimed in claim 2 wherein:
$R^1$ is methyl, ethyl, propyl, butyl, cyclopropylmethyl, cylopentyl-methyl, cyclohexyl-methyl, 2-(cyclohexyl)ethyl, cyclopentyl, cyclohexyl, cycloheptyl, phenyl, benzyl, 1-phenylethyl or 2-phenylethyl, the phenyl moiety of the latter four groups optionally bearing one or two subsituents selected from fluoro, chloro, bromo, methyl, ethyl, allyl, cyano, trifluoromethyl, nitro, amino, hydroxy, methoxy, ethoxy, methylamino, ethylamino, dimethylamino, diethylamino, methylthio, ethylthio, methylsulphinyl, ethylsulphinyl, methylsulphonyl, ethylsulphonyl, methylenedioxy and isopropylidenedioxy; $R^2$ is hydrogen, methyl, ethyl, amino, methylamino, ethylamino, propylamino or butylamino; $R^6$ is methyl, ethyl, amino, methylamino, ethylamino, propylamino or butylamino; $R^3$ and $R^4$ are independently selected from hydrogen, methyl, ethyl, phenyl, the latter optionally bearing one or two substituents selected from chloro, bromo, methyl, ethyl, methoxy and ethoxy; R5 is hydrogen, methyl, ethyl, allyl, but-2-enyl or 2-methyl-2-propenyl;
—AZB—is tetramethylene, ethyleneoxyethylene, ethyleneoxytrimethylene, ethylenethioethylene, pentamethylene, hexamethylene, ethylenecarbonylethylene, ethylene(ethylenedioxymethylene)ethylene and groups of the formula —CH$_2$CH$_2$NRCH$_2$CH$_2$—and —CH$_2$CH$_2$NRCH$_2$CH$_2$—in which R is methyl, ethyl, propyl, butyl or phenyl, the latter optionally bearing a substituent selected from fluoro, chloro, bromo, methyl, ethyl, methoxy and ethoxy.

4. A compound as claimed in claim 3 wherein Q is selected from 4-phenylpiperazino, 4-(p-chlorophenyl)-piperazino, piperidino, 3-methylpiperidino, 4-phenylpiperidino, 3,3-dimethylpiperidino, morpholino, hexamethyleneimino, 3-ethylpiperidino, 3,5-dimethylpiperidino, 3-n-propylpiperidino, 2-methylpiperidino, (4,4-ethylenedioxy)piperidino and p-methylphenylpiperidino.

5. A compound of the formula IV

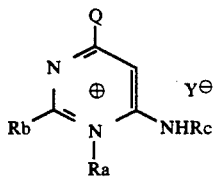

wherein: Ra is (1–4C)alkyl; Rb is (1–4C)alkyl; Rc is (1–4C)alkyl; Q is a group of formula II selected from 4-phenylpiperazino, 4-(p-chlorophenyl)piperazino, piperidino, 3-methylpiperidino, 4-phenylpiperidino, 3,3-dimethylpiperidino, morpholino, hexamethyleneimino, 3-ethylpiperidino, 3,5-dimethylpiperidino, 3-n-propylpiperidino, 2-methylpiperidino, (4,4-ethylenedioxy)piperidino and 4-p-methylphenylpiperidino; or Q is a fully saturated 9- or 10-membered bicyclic group selected from perhydroindolyl, perhydroquinolyl and perhydroisoquinolyl, any of which groups may itself optionally bear one or two substituents independently selected from methyl, ethyl, phenyl, benzyl and halogenophenyl; and Y is a physiologically acceptable anion.

6. A compound as claimed in claim 5 wherein Q is a group of formula II

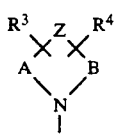

selected from 4-phenylpiperazino, 4-(p-chlorophenyl)piperazino, piperidino, 3-methylpiperidino, 4-phenylpiperidino, 3,3-dimethylpiperidino, morpholino, hexamethyleneimino, 3-ethylpiperidino, 3,5-dimethylpiperidino, 3-n-propylpiperidino, 2-methylpiperidino, (4,4-ethylenedioxy)piperidino and 4-p-methylphenylpiperidino; or Q is a fully saturated 9- or 10-membered bicyclic group selected from perhydro-1-indolyl, perhydro-1-quinolyl and perhydro-2-isoquinolyl.

7. A compound a claimed in claim 1 wherein the pyrrimindinium cation is selected from:
1,2-dimethyl-6-methylamino-4-(4-phenylpiperidino)-pyrimidinium;
1,2-dimethyl-6-methylamino-4-(N-phenylpiperazino)-pyrimidinium;
1,2-dimethyl-6-methylamino-4-(piperidino)-pyrimidinium;
1,2-dimethyl-6-methylamino-4-(3,3-dimethylpiperidino)pyrimidinium;
1,2-dimethyl-6-methylamino-4-(3-methylpiperidino)-pyrimidinium;
1,2-dimethyl-6-methylamino-4-(2-methylpiperidino)-pyrimidinium;
2-amino-1,6-dimethyl-4-(4-phenylpiperidino)-pyrimidinium;
1,2-dimethyl-6-methylamino-4-(3-ethylpiperidino)-pyrimidinium;
2-ethyl-1-methyl-6-methylamino-4-(3-methylpiperidino)pyrimidinium;
2-ethyl-1-methyl-6-ethylamino-4-(3-methylpiperidino)-pyrimidinium; and
1,2-dimethyl-6-methylamino-4-(perhydro-1-isoquinolyl)pyrimidinium;

and Y is a physiologically-acceptable counter-ion.

8. A compound as claimed in claim 1 wherein the physiologically-acceptable counter anion Y is selected from halide, sulphate, phosphate, nitrate, acetate, citrate, fumarate, succinate, trifluoroacetate, methosulphate and p-toluenesulphonate.

9. A compound as defined by formula IIIa or IIIb

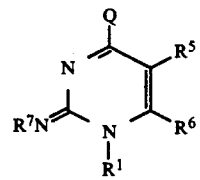

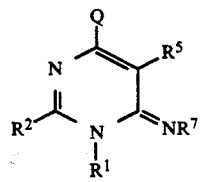

(or a tautomeric form thereof), in which $R^1$ is (1–10C)alkyl, (3–8C)cycloalkyl, (3–8C)cycloalkyl(1–4C)alkyl, phenyl or phenyl(1–4C)alkyl, the phenyl moiety of the latter two optionally bearing one or more substituents independently selected from halogeno, (1–4C)alkyl, (3–6C)alkenyl, (1–4C)alkoxy, cyano, trifluoromethyl, nitro, amino, hydroxy, (1–4C)alkylamino, dialkylamino of up to six carbon atoms, (1–4C)alkylthio, (1–4C)alkylsulphinyl, (1–4C)alkylsulphonyl and (1–4C)alkylenedioxy; $R^2$ is hydrogen, (1–4C)alkyl, amino or (1–4C)alkylamino; $R^6$ is (1–4C)alkyl, amino or (1–4C)alkylamino; Q is a group of formula II,

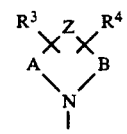

in which case $R^3$ and $R^4$ are independently hydrogen, (1–4C)alkyl, phenyl or benzyl, the phenyl moiety of the latter two optionally bearing one or two substituents selected from (1–4C)alkyl, (1–4C)alkoxy and halogeno; $R^5$ is hydrogen, (1–4C)alkyl or (2–4C)alkenyl; A and B are independently ethylene or trimethylene; Z is a direct bond between A and B, or an oxy, thio, carbonyl, methylene, ethylenedioxymethylene, ethylidene, or isopropylidene link, or Z is a group of the formula =NM in which M is hydrogen, (1–6C)alkyl, phenyl or benzyl, the phenyl moiety of the latter two optionally bearing one or two substituents selected from (1–4C)alkyl, (1–4C)alkoxy and halogeno; or Q represents a fully saturated 9- or 10-membered bicyclic ring system containing one nitrogen as the only heteroatom, Q being attached through said nitrogen to the remainder of said amino pyrimidine derivative, which Q is unsubstituted or is substituted by one or two substituents selected from (1–4C)alkyl, phenyl or benzyl, the phenyl moiety of the latter two optionally bearing one or two substituents selected from (1–4C)alkyl, (1–4C)alkoxy and halogeno; and $R^7$ stands for (1–4C)alkyl or hydrogen.

10. A compound of formula IVa

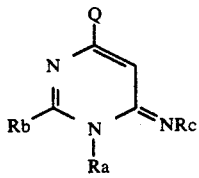
(IVa)

(or a tautomeric form thereof), in which Ra is (1–4C)alkyl; Rb is (1–4C)alkyl; Rc is (1–4C)alkyl; Q is a group of formula II selected from 4-phenyl-piperazino, 4-(p-chlorophenyl)piperazino, piperidino, 3-methylpiperidino, 4-phenylpiperidino, 3,3-dimethylpiperidino, morpholino, hexamethyleneimino, 3-ethylpiperidino, 3,5-dimethylpiperidino, 3-n-propylpiperidino, 2-methylpiperidino, (4,4-ethylenedioxy)piperidino and 4-p-methylphenylpiperidino or Q is a fully saturated 9- or 10-membered bicyclic group selected from perhydroindolyl, perhydroquinolyl and perhydroisoquinolyl, any of which groups may itself optionally bear one or two substituents independently selected from methyl, ethyl, phenyl, benzyl and halogenophenyl.

11. A pharmaceutical composition useful in modulating the action of the sino atrial node comprising an effective amount of an active ingredient selected from a compound as claimed in any one of claims 1, 5, 9 or 10 together with or in admixture with a pharmaceutically-acceptable diluent or carrier.

12. A method of modulating the action of the sino-atrial node in a warm-blooded animal requiring such treatment which comprises administering to said animal an effective amount of a pharmacologically active agent selected from the group consisting of compounds having the formulae IIIa or IIIb (or a tautomeric form thereof) as claimed in claim 9.

13. A method of modulating the action of the sino-atrial node in a warm-blooded animal requiring such treatment which comprises administering to said animal an effective amount of a pharmacologically active agent consisting of a non-ionic form of a compound having the formula IVa as claimed in claim 10.

14. A method of modulating the action of the sino-atrial node in a warm-blooded animal requiring such treatment which comprises administering to said animal an effective amount of a pharmacologically active agent consisting of a compound of the formula I as claimed in claim 1.

* * * * *